(12) United States Patent
Marrano et al.

(10) Patent No.: US 10,351,378 B2
(45) Date of Patent: Jul. 16, 2019

(54) APPARATUE FOR CONTROLLING MOVEMENT OF A SUBSTRATE

(71) Applicant: Kimberly-Clark Worldwide, Inc., Neenah, WI (US)

(72) Inventors: Stephen A. Marrano, Oshkosh, WI (US); Daniel M. Nussbaum, Neenah, WI (US); Scott C. Locy, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 15/780,449

(22) PCT Filed: Dec. 13, 2016

(86) PCT No.: PCT/US2016/066355
§ 371 (c)(1),
(2) Date: May 31, 2018

(87) PCT Pub. No.: WO2017/106173
PCT Pub. Date: Jun. 22, 2017

(65) Prior Publication Data
US 2018/0354736 A1      Dec. 13, 2018

Related U.S. Application Data

(60) Provisional application No. 62/269,604, filed on Dec. 18, 2015.

(51) Int. Cl.
*B65H 23/032* (2006.01)
*B41J 11/00* (2006.01)
(Continued)

(52) U.S. Cl.
CPC ........ *B65H 23/0322* (2013.01); *B41J 11/005* (2013.01); *B41J 11/0055* (2013.01); *B65H 20/06* (2013.01); *B65H 20/10* (2013.01); *B65H 2404/72* (2013.01); *B65H 2406/32* (2013.01); *B65H 2601/272* (2013.01)

(58) Field of Classification Search
CPC ........ B65H 9/04; B65H 9/08; B65H 2404/72; B65H 23/0322; B41J 11/005; B41J 11/0055
See application file for complete search history.

(56) References Cited

U.S. PATENT DOCUMENTS 5,377,966 A * 1/1995 Ohmori ............... B65H 31/20
271/223
5,454,648 A * 10/1995 Lee ..................... B41J 13/10
271/240
(Continued)

FOREIGN PATENT DOCUMENTS

DE          19929269 A1     12/2000
DE          19929317 A1     12/2000
WO       WO09072199 A1      6/2009

*Primary Examiner* — Jeremy R Severson
(74) *Attorney, Agent, or Firm* — Kimberly-Clark Worldwide, Inc.

(57) ABSTRACT

An apparatus can control the movement of a substrate through a manufacturing process. The apparatus can transport the substrate in the machine direction of the manufacturing process and can control the movement of the substrate in the cross-machine direction as well as the z-direction.

15 Claims, 3 Drawing Sheets

(51) Int. Cl.
*B65H 20/06* (2006.01)
*B65H 20/10* (2006.01)

(56) References Cited

U.S. PATENT DOCUMENTS

| | | | | |
|---|---|---|---|---|
| 5,478,163 A | * | 12/1995 | Flugge | B41J 11/005 400/23 |
| 5,897,258 A | * | 4/1999 | Wen | B41J 11/0055 271/250 |
| 6,184,972 B1 | | 2/2001 | Mizutani | |
| 6,536,894 B1 | | 3/2003 | Rasmussen | |
| 6,647,883 B1 | | 11/2003 | McNeil | |
| 6,869,176 B2 | * | 3/2005 | Saito | B41J 11/005 347/101 |
| 8,292,395 B2 | | 10/2012 | Ben-Zur | |
| 8,292,421 B2 | * | 10/2012 | Mandel | B41J 11/0085 347/101 |
| 8,317,315 B2 | | 11/2012 | Hoover | |
| 8,636,352 B2 | * | 1/2014 | Ito | B41J 11/005 347/101 |
| 2006/0071385 A1 | | 4/2006 | Berset | |
| 2007/0239126 A1 | | 10/2007 | Wilson | |
| 2010/0050940 A1 | | 3/2010 | Sahoda | |
| 2013/0052432 A1 | | 2/2013 | Koebel | |
| 2013/0126578 A1 | | 5/2013 | Yeo | |
| 2013/0289511 A1 | | 10/2013 | Warner | |

* cited by examiner

APPARATUE FOR CONTROLLING MOVEMENT OF A SUBSTRATE

RELATED APPLICATION

The present application claims priority to U.S. Provisional Application No. 62/269,604, filed on Dec. 18, 2015, the contents of which are hereby incorporated by reference in a manner consistent with the present application.

BACKGROUND OF THE DISCLOSURE

During manufacturing processes involving a substrate, the substrate is transported through the manufacturing process on a transport surface, such as a screen or belt. Many manufacturing processes are conducted at a high speed and the transportation of the substrate at a high speed can result in defects due to movement of the substrate on the transport surface or movement of the transport surface itself.

For example, the substrate, while generally moving in the machine direction of manufacture, can experience side-to-side movement, also known as cross-machine direction weave. This cross-machine direction weave can result in substrates which can be processed incorrectly as the cross-machine direction registration of the substrate will be incorrect. Such process implications can include, for example, cutting lines can be in the wrong locations or graphics can be printed in an offset manner or can be blurred. In addition to the potential of the substrate experiencing cross-machine direction weave, the substrate can also experience "bounce" in the z-direction, in other words, up-and-down movement. If the manufacturing process includes contacting the substrate with a coating, such as, for example, an ink, surfactant, adhesive, or any other transferable medium, and the substrate "bounces," the substrate could come into direct contact with the source of the transferable medium which can result in fouling of the source as well as an undesirable volume of medium transferring to the substrate. The bouncing of the substrate can also result in inaccurate machine direction placement of the transferable medium onto the substrate because the distance between the source of the transferable medium and the substrate changes. Additionally, a manufacturing process, by its very nature, usually involves multiple types of equipment which can operate at speeds which can differ from one machine to the next. The differentials in speed can result in fluctuations in the tension of the substrate. Fluctuation in tension during a manufacturing process can also be caused by any acceleration and/or deceleration of the manufacturing machinery, any fluctuation in the tension during the unwinding of the substrate as it enters the manufacturing process, as well as by the substrate itself if the substrate has a generally non-uniform shape in either the cross-machine direction or the machine direction (e.g., the substrate may have an egg shape or oval shape rather than a more square or rectangular shape). If the manufacturing process includes contacting the substrate with a coating such as described above, such fluctuations in the tension of the substrate can result in stretching or bunching of the substrate which can result in the transferable medium being incorrectly applied to the substrate.

There is a need to control the movement of a substrate while transporting the substrate through a manufacturing process. There is a need to minimize the cross-machine direction weave of a substrate while transporting the substrate through a manufacturing process. There is a need to minimize the z-direction bounce of a substrate while transporting the substrate through a manufacturing process. There is a need to control the movement of a substrate while transporting the substrate through a manufacturing process so that a transferable medium can be applied to the substrate with greater accuracy.

SUMMARY OF THE DISCLOSURE

In various embodiments, an apparatus to control the movement of a substrate in the machine direction of a manufacturing process comprises a machine direction, a cross-machine direction perpendicular to the machine direction, and a z-direction perpendicular to each of the machine direction and the cross-machine direction; a transport surface capable of moving a substrate in the machine direction and having a first major surface, an opposing second major surface, a first machine direction edge and a second machine direction edge; a first pair of transport surface guides wherein a first guide in the first pair of guides is positioned proximate to the first machine direction edge of the transport surface and the second guide in the first pair of guides is positioned proximate the second machine direction edge of the transport surface and directly opposite the first guide in the first pair of guides; a second pair of transport surface guides wherein a first guide in the second pair of guides is positioned proximate to the first machine direction edge of the transport surface and the second guide in the second pair of guides is positioned proximate the second machine direction edge of the transport surface and directly opposite the first guide in the second pair of guides; and the second pair of transport surface guides is positioned in a spaced apart relationship to the first pair of transport surface guides; wherein each of the guides in the first pair of transport surface guides and the second pair of transport surface guides limit the movement of the transport surface in the cross-machine direction and in the z-direction.

In various embodiments, each of the first and second guides of the first pair of transport surface guides and each of the first and second guides of each of the second pair of transport surface guides further comprises two separate guide units. In various embodiments, a first of the two separate guide units has a surface which can form a plane parallel with a plane formed by a machine direction edge and wherein a second of the two separate guide units has a surface which can form a plane parallel with a plane formed by the first major surface of the transport surface.

In various embodiments, each of the first and second guides of the first pair of transport surface guides and each of the first and second guides of each of the second pair of transport surface guides are each formed from a single unitary component. In various embodiments, the single unitary component has a surface which can form a plane parallel with a plane formed by a machined direction edge and has a surface which can form a plane parallel with a plane formed by the first major surface of the transport surface.

In various embodiments, a variance between a desired width of the transport surface and a finished width of the transport surface is less than ±0.025.

In various embodiments, the apparatus further comprises a coating source positioned above the transport surface in the z-direction. In various embodiments, the first pair of transport surface guides is positioned upstream in the machine direction of the coating source and the second pair of transport surface guides is positioned downstream in the machine direction of the coating source. In various embodiments, the apparatus further comprises at least one additional pair of transport surface guides positioned between the first and second pair of transport surface guides. In various embodiments, the coating source applies a transferable medium to the substrate. In various embodiments, the transferable medium can be an ink, a surfactant, or an adhesive.

In various embodiments, the transport surface makes contact with at least one of the transport surface guides in the cross-machine direction of the apparatus. In various embodiments, the transport surface makes contact with an opposing pair of transport surface guides in the cross-machine direction of the apparatus.

In various embodiments, at least one aperture extends from the first major surface of the transport surface to the second major surface of the transport surface. In various embodiments, the apparatus further comprises a vacuum source positioned below the transport surface in the z-direction.

Figure 1:
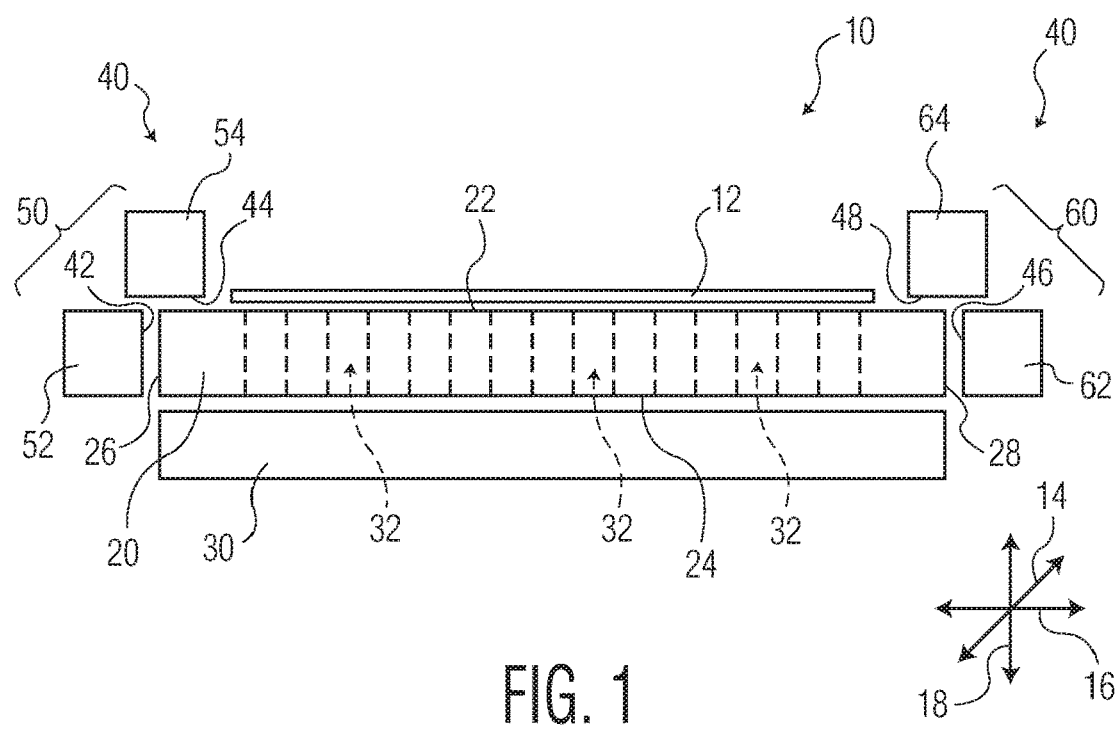
FIG. 1 is a schematic end view of an exemplary embodiment of an apparatus.

Repeat use of reference characters in the present specification and drawings is intended to represent the same or analogous features or elements of the disclosure.

DETAILED DESCRIPTION OF THE DISCLOSURE

The present disclosure is generally directed towards an apparatus that can control the movement of a substrate through a manufacturing process. The apparatus can transport the substrate in the machine direction of the manufacturing process and can control the movement of the substrate in the cross-machine direction as well as the z-direction.

A substrate whose movement can be controlled by the apparatus described herein can be a woven, nonwoven, or film material. The term "woven" refers herein to a material which is formed with the aid of a textile kitting or weaving process. The term "nonwoven" refers herein to a material which is formed without the aid of a textile weaving or knitting process. The material can have a structure of individual fibers, filaments, or threads (collectively referred to as "fibers") which can be interlaid, but not in an identifiable manner as in a knitted fabric. Nonwoven material can be formed from many processes such as, but not limited to, meltblowing processes, spunbonding processes, carded web processes, etc. The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

Figure 2:
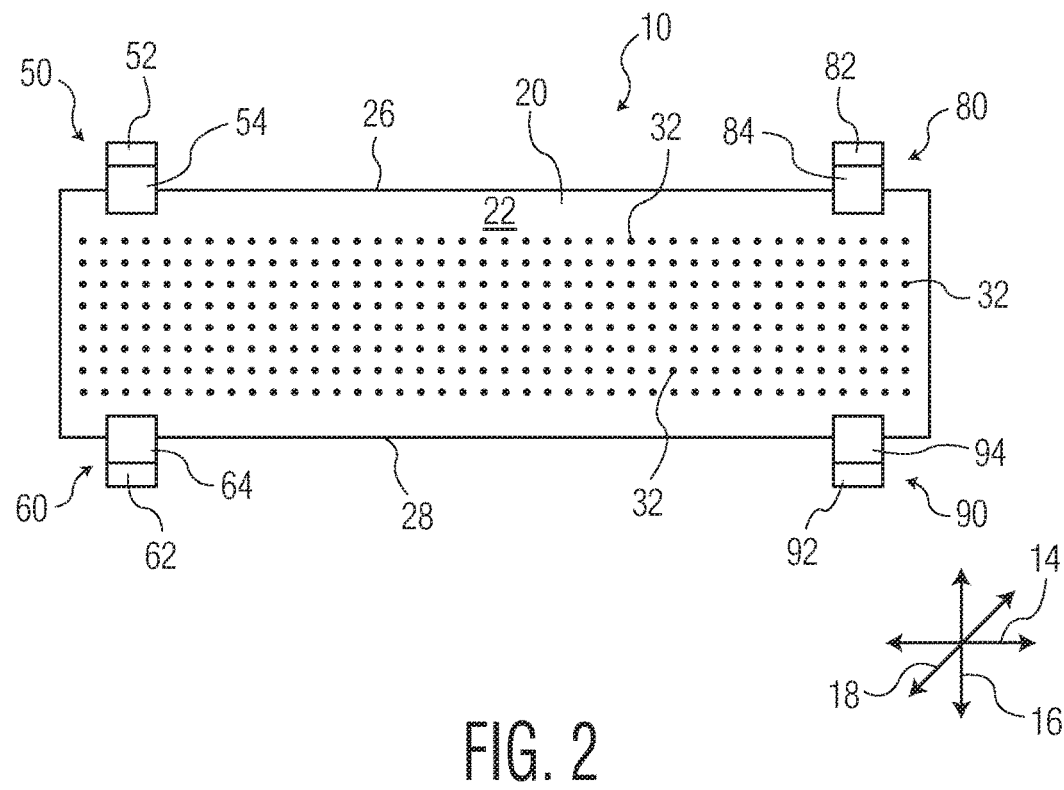
FIG. 2 is a top down view of the exemplary embodiment of the apparatus of FIG. 1.

Referring to FIGS. 1 and 2, a schematic end view of an exemplary apparatus 10 is illustrated in FIG. 1 and a top view of the apparatus 10 of FIG. 1 is illustrated in FIG. 2.

The apparatus 10 can have a transport surface 20 which can have a first major surface 22, a second major surface 24, and first machine direction edge 26 and a second machine direction edge 28 opposite the first machine direction edge 26. A substrate 12 can be positioned on the first major surface 22 of the transport surface 20 and the transport surface 20 of the apparatus 10 can be capable of moving the substrate 12 in the machine direction 14. In various embodiments, the transport surface 20 can be a surface such as a belt or screen. The transport surface 20 can be formed of any material deemed suitable, such as, for example, polyvinyl chloride, polyurethane, polyethylene, polyolefin, rubber, silicone, nylon, thermoplastic polyester, plastic compounds, gum rubber, mesh material, felt, and combinations thereof.

In various embodiments, the transport surface 20 can be configured in any manner deemed suitable and as known in the art to provide machine direction movement and transport of a substrate positioned thereon. For example, in various embodiments, the transport surface 20 can be a belt that loops around at least two rollers (not shown). In such embodiments, the transport surface 20 can be stretched tightly over the rollers such that if either roller turns, the transport surface 20 will move as well.

The apparatus can have at least two pairs of transport surface guides. Referring to FIG. 1, a first pair 40 of transport surface guides, 50 and 60, is illustrated. As illustrated in FIG. 1, the first guide 50 in the first pair 40 of transport surface guides is positioned proximate to the first machine direction edge 26 of the transport surface 20 and the second guide 60 in the first pair 40 of transport surface guides is positioned proximate to the second machine direction edge 28 of the transport surface 20 and opposite the first guide 50 in the first pair 40 of transport surface guides.

In various embodiments, such as illustrated in FIG. 1, the first guide 50 can include two separate guide units 52 and 54, and the second guide 60 can include two separate guide units, 62 and 64. Guide units, 52 and 62, can be positioned such that they are proximate the machine direction edges, 26 and 28, respectively, of the transport surface 20 in the cross-machine direction of the apparatus 10. In various embodiments, guide units, 52 and 62, can each have a surface, 42 and 46, respectively, proximate the machine direction edges, 26 and 28, respectively, of the transport surface 20 which can form a plane that is parallel with the plane formed by the machine direction edges, 26 and 28, of the transport surface 20. Guide units, 54 and 64, can be positioned such that they are proximate the machine direction edges, 26 and 28, respectively, of the transport surface 20 in the z-direction of the apparatus 10. In various embodiments, guide units, 54 and 64, can each have a surface, 44 and 48, respectively, proximate the machine direction edges, 26 and 28, respectively, of the transport surface 20, which can form a plane that is parallel with the plane formed by the first major surface 22 of the transport surface 20.

The transport surface 20 can have any width dimension between guide units, 52 and 62, as deemed suitable. To limit cross-machine direction weave of a substrate 12 positioned upon the first major surface 22 of the transport surface 20, in various embodiments, the transport surface 20 has a width dimension which can position the transport surface 20 between the guide units, 52 and 62, and as close to the guide units, 52 and 62, as deemed possible. In various embodiments, the transport surface 20 can have a width dimension such that the transport surface 20 may come into contact with at least one guide unit, such as guide units 52 and 82. The guide units, such as guide units 52 and 82, can serve as a positive locating device for the transport surface 20 which can assist with minimizing the cross-machine direction weave of the transport surface 20 and, ultimately, of the substrate 12. In various embodiments, the transport surface 20 can have a width dimension such that the transport surface 20 may come into contact with opposing guide units, such as guide units 52 and 62. As the transport surface 20 may come into contact with a guide unit, such as guide unit 52, 62, 82 and/or 92, the guide unit can roll with the movement of the transport surface 20. If the guide unit were completely stationary and without a rolling capability, friction would build up between the guide unit and the transport surface 20 causing fouling of the transport surface 20. To minimize such fouling, the guide unit remains in its designated location, but rolls with the movement of the transport surface 20.

To maintain the proper distance between the guide units, 52 and 62, and the machine direction edges, 26 and 28, of the transport surface 20, the machine direction edges, 26 and 28, of the transport surface 20 can be finished (e.g., edge slit and/or ground) to produce a finished width dimension of the transport surface 20 such that the tolerance needed between the machine direction edges, 26 and 28, and the surfaces, 42 and 46, of the guide units, 52 and 62, respectively, can be minimal. In various embodiments, the variance between the desired width dimension of the transport surface 20 and a finished width dimension of the transport surface 20 can be less than ±0.025 inch. In various embodiments, the variance between the desired width dimension of the transport surface 20 and a finished width dimension of the transport surface 20 can be less than ±0.020 inch. In various embodiments, the variance between the desired width dimension of the transport surface 20 and a finished width dimension of the transport surface 20 can be less than ±0.015 inch. In various embodiments, the variance between the desired width dimension of the transport surface 20 and a finished width dimension of the transport surface 20 can be ±0.010 inch. It is believed that minimal variance between the desired width dimension of the transport surface 20 and the finished width dimension of the transport surface 20 can allow for closer positioning of the guide units, 52 and 62, to the machine direction edges, 26 and 28, of the transport surface 20. The closer positioning of the guide units, 52 and 62, to the machine direction edges, 26 and 28, of the transport surface 20 can result in minimal space in which the transport surface 20 may weave in the cross-machine direction which can result, therefore, in minimal weave in the cross-machine direction of a substrate 12 positioned on a first major surface 22 of the transport surface 20.

In various embodiments, the apparatus 10 can also limit movement of the substrate 12 in the z-direction 18. The transport surface 20 can be provided with at least one aperture 32 which can extend from the first major surface 22 of the transport surface 20, through the material forming the transport surface 20, and to the second major surface 24 of the transport surface 20. In such embodiments, a vacuum source 30 can be positioned below the transport surface 20 and can draw air, in the machine direction 14, through the at least one aperture 32. The air can move from above, in the z-direction 18, the transport surface 20, and can be pulled through the at least one aperture 32 from the first major surface 22 and through and to the second major surface 24 of the transport surface 20. When a substrate 12 is positioned on the first major surface 22 of the transport surface 20, the vacuum source 30 can pull the substrate 12 in the z-direction towards the transport surface 20. The vacuum source 30 can be calibrated to pull the substrate 12 and hold the substrate 12 against the transport surface 20.

Referring to FIG. 2, a top view of the apparatus of FIG. 1 is illustrated. As can be seen in FIG. 2, the apparatus 10 can have a second pair of transport surface guide, 80 and 90. Similar to the first pair 40 of transport surface guides, 50 and 60, the first guide 80 in the second pair of transport surface guides is positioned proximate to the first machine direction edge 26 of the transport surface 20 and the second guide 90 in the second pair of transport surface guides is positioned proximate to the second machine direction edge 28 of the transport surface 20 and opposite the first guide 80 in the second pair of transport surface guides. The second pair of transport surface guides, 80 and 90, is also positioned a distance away from the first pair of transport surface guides, 50 and 60. Similar to the first part of transport surface guides, 50 and 60, the second pair of transport surface guides, 80 and 90, can each include two separate guide units such as guide units 82, 84, 92 and 94, respectively. Transport surface guides, 80 and 90, can include guide units, 82 and 92, respectively, which can be positioned such that they are proximate the machine direction edges, 26 and 28, respectively of the transport surface 20 in the cross-machine direction 16 of the apparatus 10. In various embodiments, guide units, 82 and 92, can each have a surface proximate the machine direction edges, 26 and 28, respectively, of the transport surface 20 which can form a plane that is parallel to a plane formed by the machine direction edges, 26 and 28, of the transport surface 20. Guide units, 84 and 94, can be positioned such that they are proximate the machine direction edges, 26 and 28, respectively, of the transport surface 20 in the z-direction 18 of the apparatus 10. In various embodiments, guide units, 84 and 94, can each have a surface proximate the machine direction edges, 26 and 28, respectively, of the transport surface 20, which can form a plane that is parallel with the plane formed by the first major surface 22 of the transport surface 20.

In combination, therefore, the apparatus 10 can control the movement of a substrate 12 in a manufacturing process. As described herein, the apparatus can be operated at high speed in a manufacturing process and the movement of a substrate 12 can be controlled in the cross-machine direction 16 and in the z-direction 18 as the substrate is being transported in the machine direction 14 during a manufacturing process. The apparatus can have a pair of transport guides units, such as guide units 50 and 60, which are positioned proximate to the machine direction edges, 26 and 28, respectively, of a transport surface 20 and the guide unites, 50 and 60, can limit movement of the transport surface 20 in the cross-machine direction 16, thereby, limiting movement of the substrate 12 in the cross-machine direction 16. The same apparatus can limit movement of the substrate 12 in the z-direction 18 as the vacuum source 30 can pull the substrate 12 into closer positioning on the first major surface 22 of the transport surface 20. The vacuum source 30 can maintain the substrate 12 in such a position until it is desired that the substrate 12 not be immediately positioned on the first major surface 22 of the transport surface 20.

In various embodiments, the apparatus 10 described herein can be utilized in a variety of locations on a manufacturing production line. For example, in various embodiments, the apparatus 10 described herein can be used in connection with a coating source 100. The coating source 100 can be positioned, in the z-direction 18, above the substrate 12 in such a manner as deemed suitable such that as the substrate 12 passed beneath the coating source 100 the desired coating can be applied to the substrate 12. In various embodiments, the coating source 100 can be utilized to provide a coating of a surfactant, adhesive, ink, or any other transferable medium.

Figure 3:
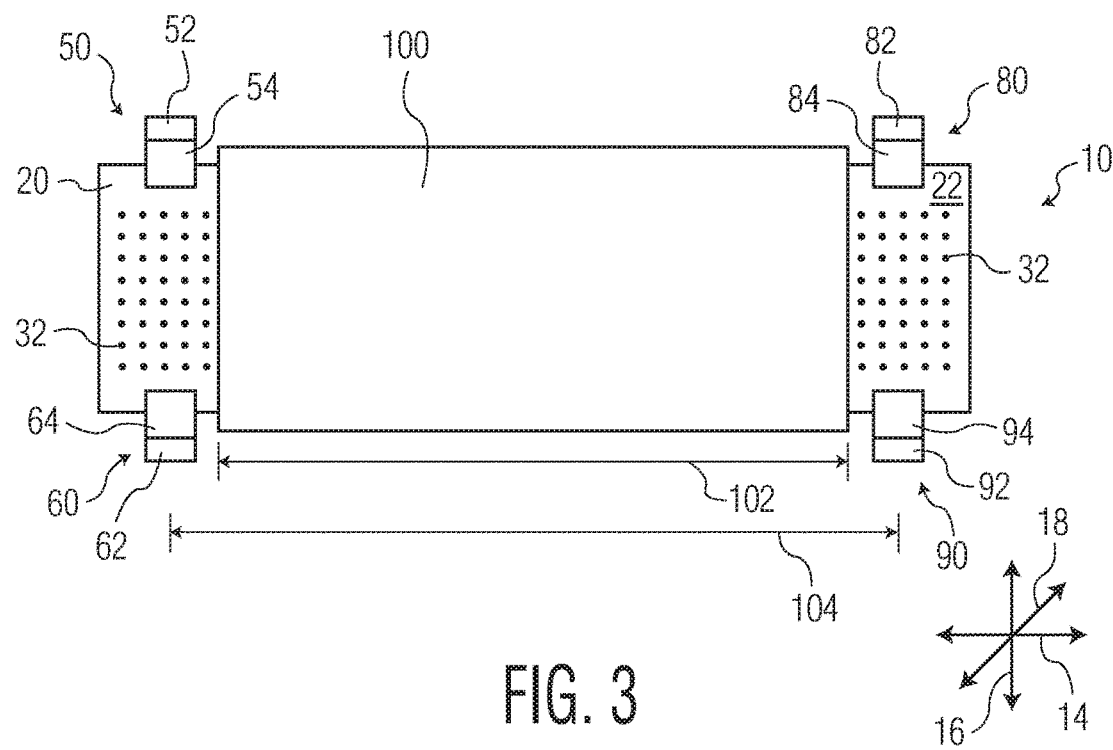
FIG. 3 is a top down view of the exemplary embodiment of the apparatus of FIG. 1 and a coating source.

Referring to FIG. 3, a coating source 100 can be positioned, in the z-direction 18, above the apparatus 10. In various embodiments, the coating source 100 can be positioned between the first pair of transport surface guides, 50 and 60, and the second pair of transport surface guides, 80 and 90. It is believed that transport surface guides, 50 and 60, positioned upstream of the coating source 100 and transport surface guides, 80 and 90, positioned downstream of the coating source 100, can help to maintain the substrate 12 in appropriate alignment through the duration of the application of the desired coating. In various embodiments, additional pairs of transport surface guides can be included in the machine direction and positioned between the first pair of transport surface guides, 50 and 60, and the second pair of transport surface guides, 80 and 90.

Figure 4:
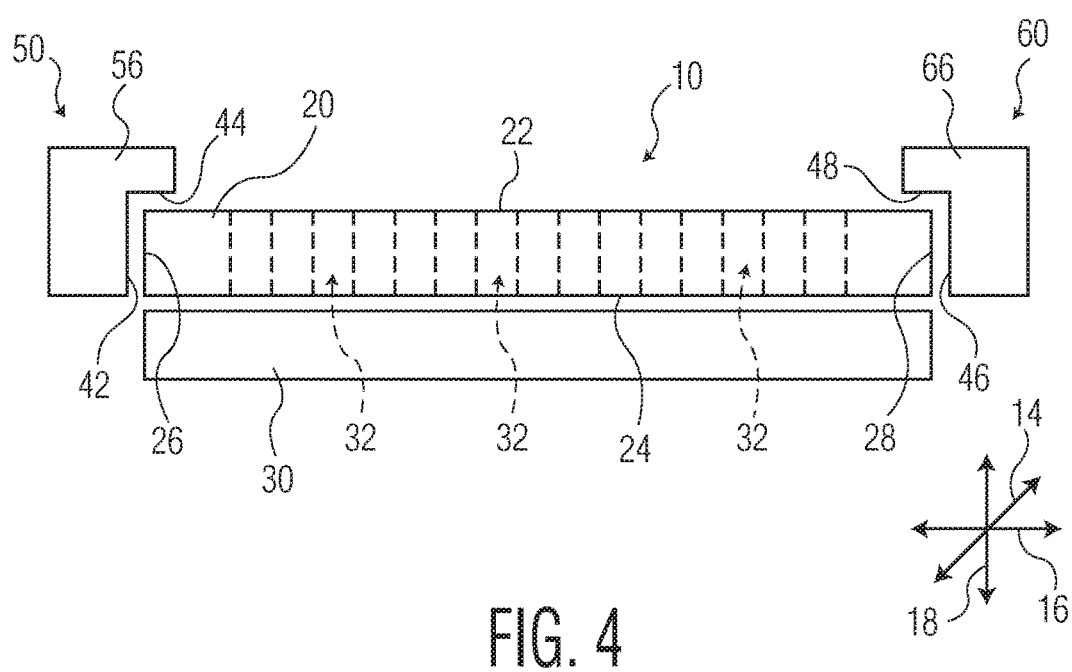
FIG. 4 is an end view of an exemplary alternative embodiment of an apparatus.
Figure 5:
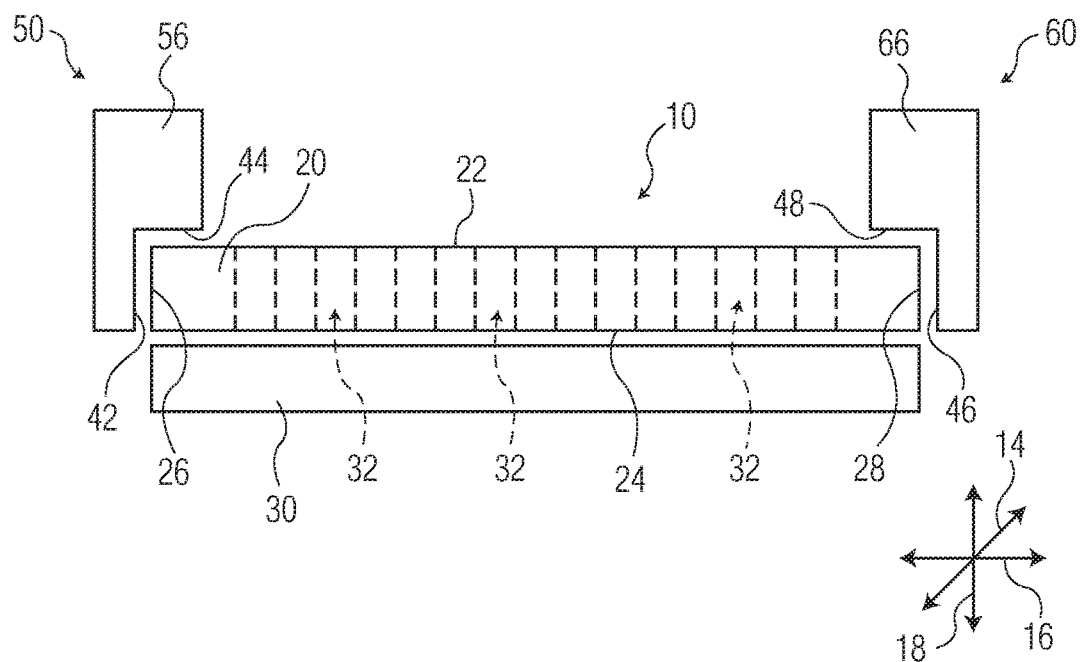
FIG. 5 is an end view of an exemplary alternative embodiment of an apparatus.
Figure 6:
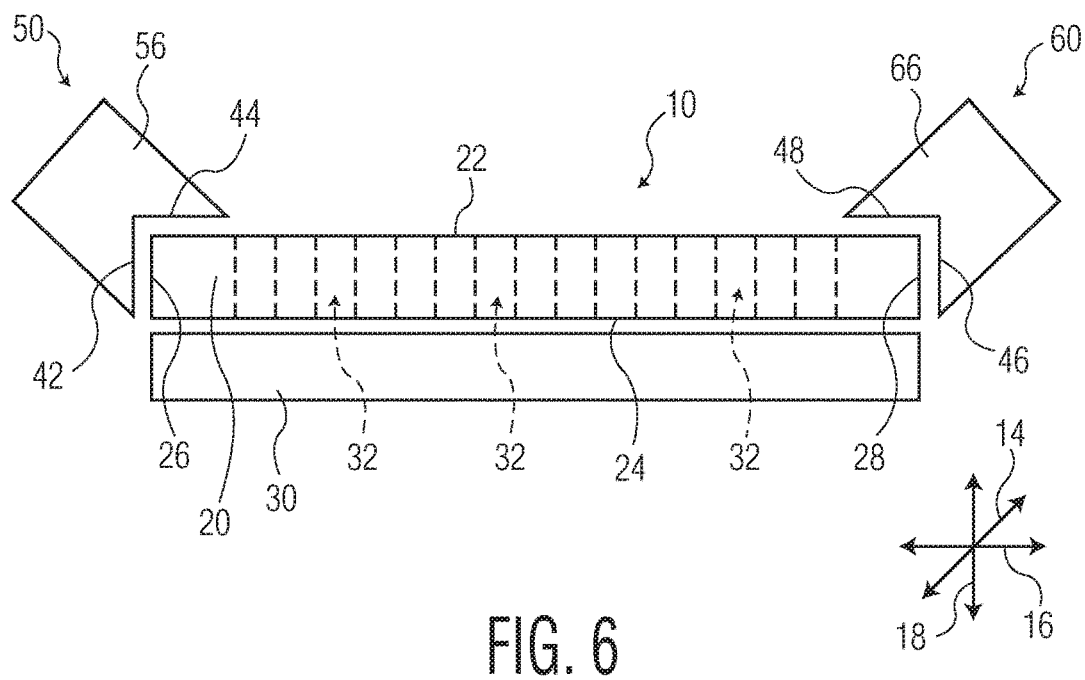
FIG. 6 is an end view of an exemplary alternative embodiment of an apparatus.

Referring to FIGS. 4, 5, and 6, in various embodiments, the transport surface guides, 50, 60, 80 and 90, can be formed from a single unitary component. For example, as illustrated in FIGS. 4, 5 and 6, the transport surface guides, 50 and 60, can be formed of a single unitary component, 56 and 66, respectively. Each single unitary component, such as 56 and 66, can have a portion positioned proximate the machine direction edges, 26 and 28, in the cross-machine direction 18 of the apparatus 10 and such portions can have a surface, 42 and 46, respectively, which can form a plane that is parallel with the plane formed by the machine direction edges, 26 and 28, respectively of the transport surface 20. Each single unitary component, such as 56 and 66, can further have a portion positioned proximate the machine direction edges, 26 and 28, respectively, of the transport surface 20 in the z-direction of the apparatus and such portions can have a surface, 44 and 48, respectively, which can form a plan that is parallel with the plane formed by the first major surface 22 of the transport surface 20 of the apparatus 10.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An apparatus to control the movement of a substrate in the machine direction of a manufacturing process, the apparatus comprising:
   a. a machine direction, a cross-machine direction perpendicular to the machine direction, and a z-direction perpendicular to each of the machine direction and the cross-machine direction;
   b. a transport surface capable of moving a substrate in the machine direction and having a first major surface, an opposing second major surface, a first machine direction edge and a second machine direction edge;
   c. a first pair of transport surface guides wherein a first guide in the first pair of guides is positioned proximate to the first machine direction edge of the transport surface and the second guide in the first pair of guides is positioned proximate the second machine direction edge of the transport surface and directly opposite the first guide in the first pair of guides;
   d. a second pair of transport surface guides wherein a first guide in the second pair of guides is positioned proximate to the first machine direction edge of the transport surface and the second guide in the second pair of guides is positioned proximate the second machine direction edge of the transport surface and directly opposite the first guide in the second pair of guides; and
   e. the second pair of transport surface guides is positioned in a spaced apart relationship to the first pair of transport surface guides;
   f. wherein each of the guides in the first pair of transport surface guides and the second pair of transport surface guides limit the movement of the transport surface in the cross-machine direction and in the z-direction.

2. The apparatus of claim 1 wherein each of the first and second guides of the first pair of transport surface guides and each of the first and second guides of each of the second pair of transport surface guides further comprises two separate guide units.

3. The apparatus of claim 2 wherein a first of the two separate guide units has a surface which can form a plane parallel with a plane formed by a machine direction edge and wherein a second of the two separate guide units has a surface which can form a plane parallel with a plane formed by the first major surface of the transport surface.

4. The apparatus of claim 1 wherein each of the first and second guides of the first pair of transport surface guides and each of the first and second guides of each of the second pair of transport surface guides are each formed from a single unitary component.

5. The apparatus of claim 4 wherein the single unitary component has a surface which can form a plane parallel with a plane formed by a machined direction edge and has a surface which can form a plane parallel with a plane formed by the first major surface of the transport surface.

6. The apparatus of claim 1 wherein a variance between a desired with of the transport surface and a finished width of the transport surface is less than ±0.025 inch.

7. The apparatus of claim 1 further comprising a coating source positioned above the transport surface in the z-direction.

8. The apparatus of claim 7 wherein the first pair of transport surface guides is positioned upstream in the machine direction of the coating source and the second pair of transport surface guides is positioned downstream in the machine direction of the coating source.

9. The apparatus of claim 7 further comprising at least one additional pair of transport surface guides positioned between the first and second pair of transport surface guides.

10. The apparatus of claim 7 wherein the coating source applies a transferable medium to the substrate.

11. The apparatus of claim 10 wherein the transferable medium can be an ink, a surfactant, or an adhesive.

12. The apparatus of claim 1 wherein the transport surface makes contact with at least one of the transport surface guides in the cross-machine direction of the apparatus.

13. The apparatus of claim 12 wherein the transport surface makes contact with an opposing pair of transport surface guides in the cross-machine direction of the apparatus.

14. The apparatus of claim 1 wherein at least one aperture extends from the first major surface of the transport surface to the second major surface of the transport surface.

15. The apparatus of claim 14 further comprising a vacuum source positioned below the transport surface in the z-direction.

\* \* \* \* \*